(12) United States Patent
Freeman et al.

(10) Patent No.: US 12,208,229 B1
(45) Date of Patent: Jan. 28, 2025

(54) METHOD OF JOINING STERILE CONNECTORS

(71) Applicant: Unicorn Biotechnologies Ltd., Sheffield (GB)

(72) Inventors: George Leonard Freeman, Knaresborough (GB); Albert Houghton, Sheffield (GB); Carl Heimann, Sheffield (GB); Jakub Jasik, Sheffield (GB); Adam Mitchell, Sheffield (GB); Poppy Culshaw, Sheffield (GB); Adam Glen, Sheffield (GB)

(73) Assignee: Unicorn Biotechnologies Ltd., Sheffield (GB)

( * ) Notice: Subject to any disclaimer, the term of this patent is extended or adjusted under 35 U.S.C. 154(b) by 0 days.

(21) Appl. No.: 18/799,903

(22) Filed: Aug. 9, 2024

Related U.S. Application Data

(63) Continuation of application No. 18/518,973, filed on Nov. 25, 2023.

(60) Provisional application No. 63/602,571, filed on Nov. 25, 2023.

(51) Int. Cl.
*A61M 39/18* (2006.01)

(52) U.S. Cl.
CPC .................................. *A61M 39/18* (2013.01)

(58) Field of Classification Search
CPC ....... A61M 39/00; A61M 39/10; A61M 39/08
See application file for complete search history.

(56) References Cited

U.S. PATENT DOCUMENTS

| | | | |
|---|---|---|---|
| 4,019,512 A * | 4/1977 | Tenczar | A61M 39/14 604/905 |
| 10,946,183 B2 * | 3/2021 | Faldt | A61M 39/16 |
| 2003/0030272 A1 * | 2/2003 | Johnson | F16L 29/00 285/70 |

* cited by examiner

*Primary Examiner* — Chelsea E Stinson
*Assistant Examiner* — Hamza A Darb
(74) *Attorney, Agent, or Firm* — Eric P. Mirabel

(57) ABSTRACT

Disclosed is a convenient joining of tubing in a secure, leak-free connection, suitable for aseptic fluid transfer, wherein two holders each have a channel designed to house tubing and each holder has a mating surface at one end of the channel. The ends of the respective tubing closest to the mating surfaces are fitted with male and female hollow connectors. Tape is attached to the region of the connectors near the tubing and/or to the tubing itself. After the holders are joined, the ends of the tape are pulled to advance the male and female connectors to mate and form a secure connection.

15 Claims, 10 Drawing Sheets

METHOD OF JOINING STERILE CONNECTORS

BACKGROUND

The need for sterile fluid pathways is essential in healthcare, pharmaceuticals and biotechnology, where contamination can lead to significant financial losses and result in negative health outcomes including death. In these fields, joining two independent and sterile fluidic systems to allow the transfer of fluids between these systems without introducing contamination is often necessary, both in manufacturing and the use of fluid systems for patients.

Such connections are typically made under non-sterile conditions with exposure to the surrounding environment, such as by tube welding (see e.g., Biowelder® TC Sterile Welding Device by Sartorius), which is commonly used to create a fluidic connection for blood transfusions. However, these connections are permanent, difficult to automate, and expensive.

With a single use sterile connector, the connectors typically rely on mating compliant surfaces to create a seal before peeling away an internal tab that exposes the interior of each tube to the other, allowing for a sterile fluid connection to be made. However, these connections are permanent and generally more appropriate for larger diameter tubing. U.S. Pat. No. 4,019,512 discloses a tape layer sealing a device that houses connectors inside, but does not disclose using removal of the tape to force the connectors together.

Tube welders and tape connectors establish non-reversible connections, consequently the connection must either be kept in place until the need for the connection has ended, or multiple redundant paths must be kept together with a means of sealing the established connection before breaking it, in order to avoid contamination of the fluid network.

Sterilization approaches that make use of chemical agents permit sterile breaking and re-establishing sterile connections, however such use can introduce these agents as contaminants themselves into the fluid network. Also use of chemical agents, an external sterile environment or an external mechanism (such as tube welders), are less suitable to automation due to the complexity of the action and the need to apply the process to a potentially large number of tubes.

For non-sterile connectors, one can make the connection in a sterile environment. But this can be both impractical and introduces added complexity and cost.

Waste that can be considered chemically or biologically hazardous is currently subject to autoclaving and safe disposal in a manner that does not consider the environmental impact. Current sterile connectors are mechanically complex and not designed for disassembly, therefore, even components that may not be considered biologically hazardous are subject to the same expensive waste treatment process.

Robotic automation has become increasingly prevalent in various industries due to its precision, efficiency, and ability to minimise human intervention. In applications where aseptic fluid transfer is vital, there is a growing need for semi-sterile connectors that can be seamlessly integrated into automated processes, allowing for repeated, reliable connections and disconnections while maintaining sterility.

The development of a semi-sterile connector and method that meets these criteria has the potential to revolutionize industries reliant on aseptic fluid transfer. Such an innovation would not only improve the efficiency of operations but also enhance product quality and safety by reducing the risk of contamination during fluid transfer, particularly in high-throughput manufacturing processes, clinical settings, and laboratory environments.

SUMMARY

This invention includes a convenient joining of tubing in a secure, leak-free connection, suitable for aseptic fluid transfer, wherein two holders each have a channel designed to house tubing and each holder has a mating surface at one end of the channel. The ends of the respective tubing closest to the mating surfaces are fitted with male and female hollow connectors. Tape is attached to the region of the connectors near the tubing and/or to the tubing itself. After the holders are joined, the ends of the tape are pulled to advance the male and female connectors to mate and form a secure connection.

In a preferred embodiment, two lengths of tape are used for each tubing and connector, such that the tubing and/or the connectors are held between the two lengths of tape. The ends of the tape can include a backing to make it easier to initiate pulling them apart. The male and female connectors are advanced toward each other by pulling apart the two lengths of tape. Keeping the tubing between layers of tape in this manner helps the fluid in the tubing maintain sterility or semi-sterility during connection.

BRIEF DESCRIPTION OF DRAWINGS

FIG. 7B shows the joined holders of FIG. 7A with the pinch valves open, allowing fluid to flow through.

DETAILED DESCRIPTION

Figure 1A:
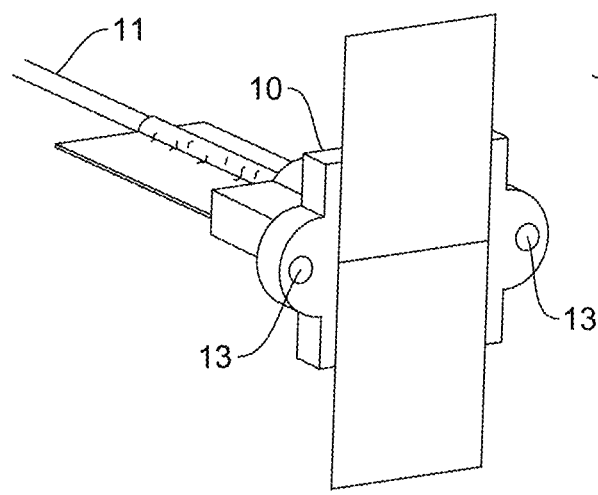
FIG. 1A is an elevational view of a holder of the invention with a male connector withdrawn and not visible.
Figure 1B:
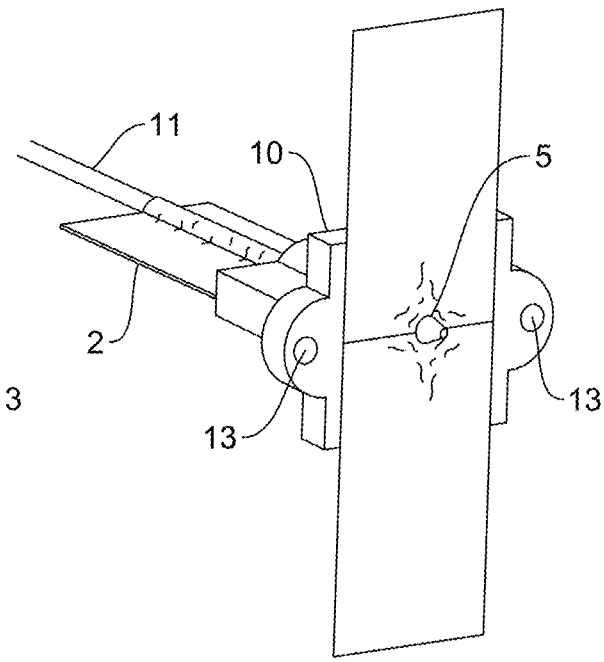
FIG. 1B is an elevational view of the holder of FIG. 1A with the male connector extended in position to mate.
Figure 1C:
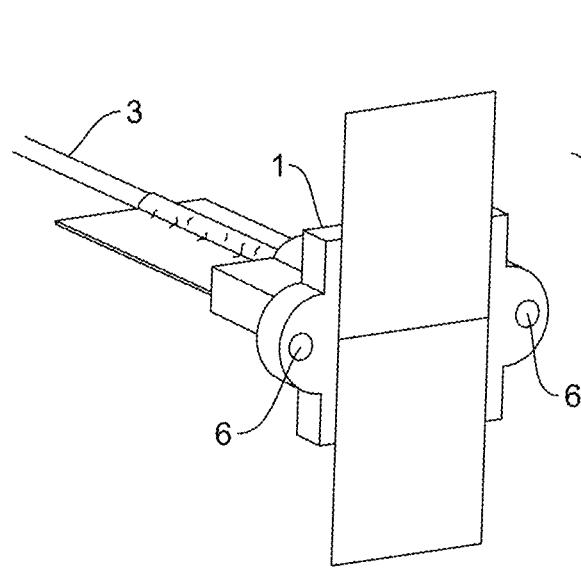
FIG. 1C is an elevational view of a holder of the invention with a female connector withdrawn and not visible.
Figure 1D:
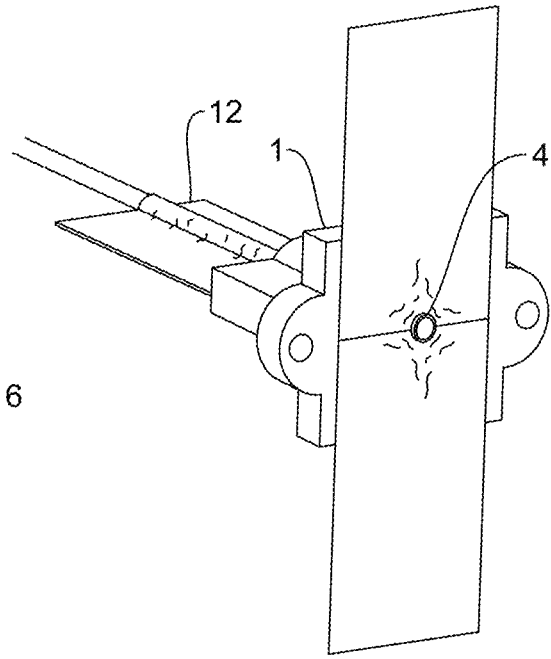
FIG. 1D is an elevational view of the holder of FIG. 1C with the female connector in position to mate.
Figure 2A:
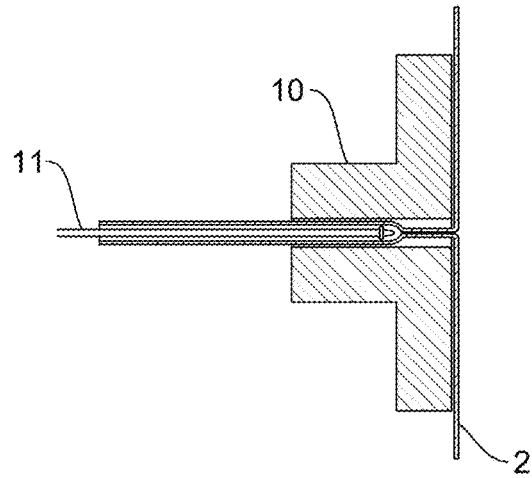
FIG. 2A is a cross-sectional view of the holder of FIG. 1A showing the male connector before extension.
Figure 2B:
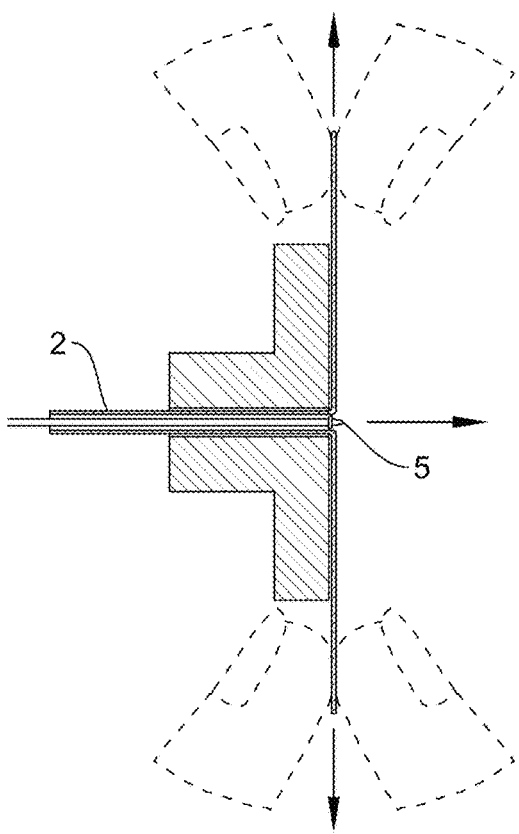
FIG. 2B is a cross-sectional view of the holder of FIG. 2A showing the male connector after extension.
Figure 2C:
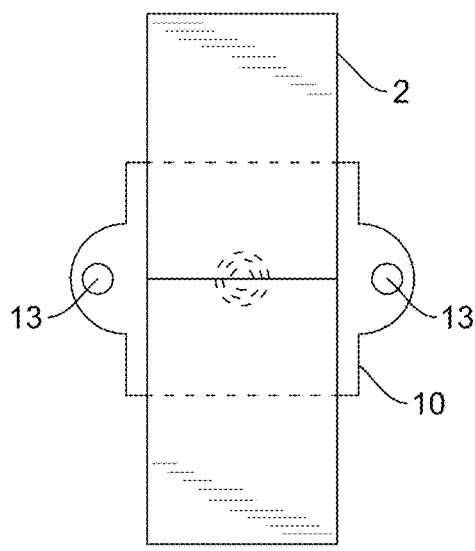
FIG. 2C is an elevational view of the holder of FIG. 2A showing the male connector after extension.
Figure 2D:
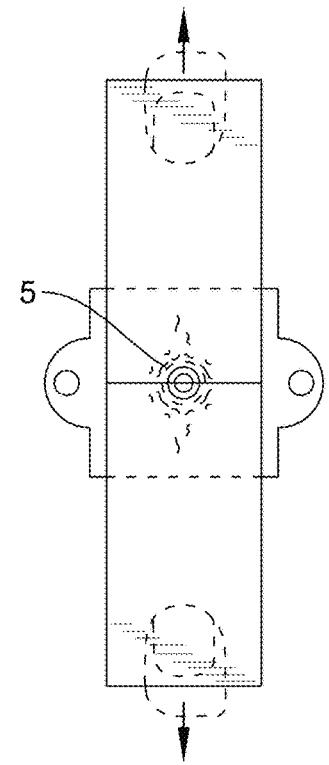
FIG. 2D is an elevational view of the holder of FIG. 2B showing the male connector after extension.
Figure 3A:
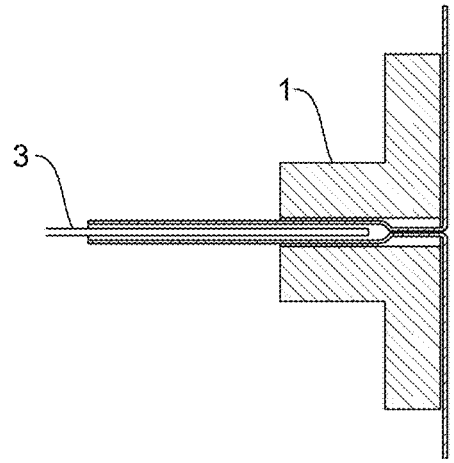
FIG. 3A is a cross-sectional view of a holder of FIG. 1C with a female connector withdrawn and not visible.
Figure 3B:
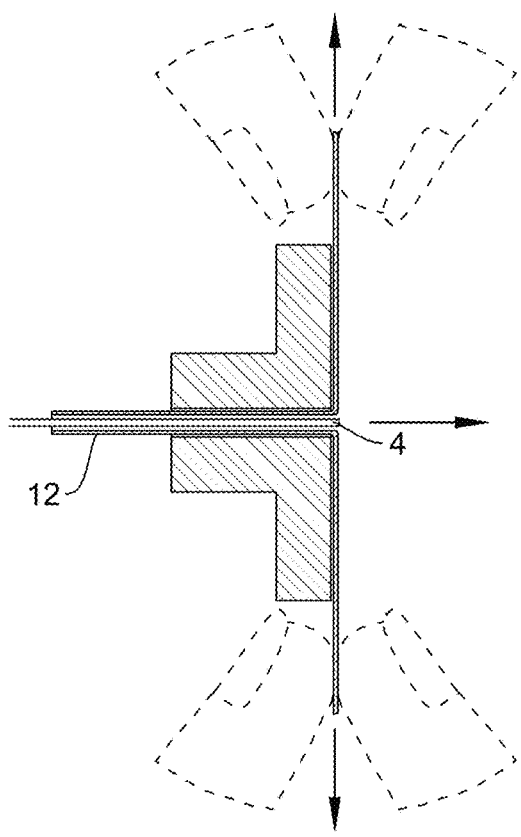
FIG. 3B is a cross-sectional view of the holder of FIG. 3A with the female connector positioned for mating.
Figure 3C:
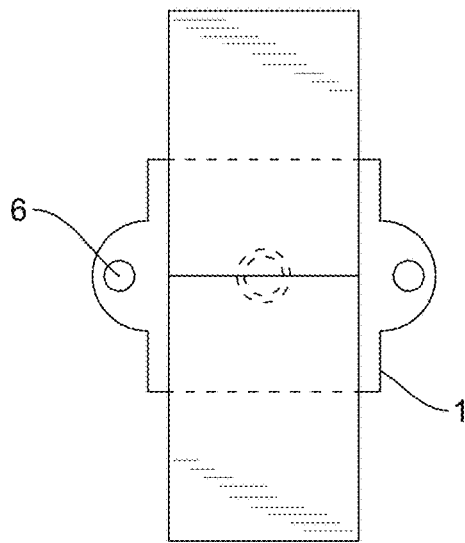
FIG. 3C is an elevational view of a holder of FIG. 3A with the female connector withdrawn and not visible.
Figure 3D:
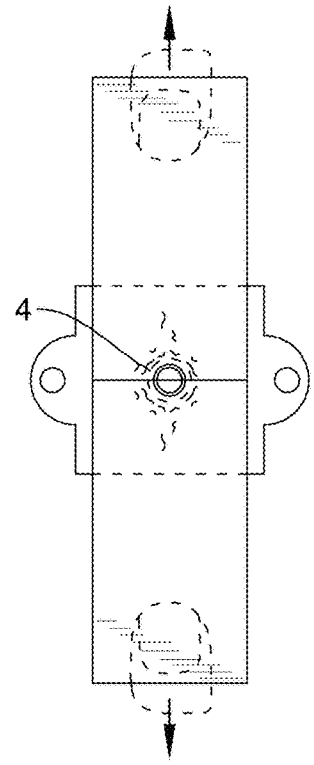
FIG. 3D is an elevational view of a holder of FIG. 3B with the female connector positioned for mating.

Referring to FIG. 1, holders 1 and 10 have channels (not shown) housing tubing 11 and 3, respectively. Tubing 11 has a male connector 5 at its end and tubing 3 has a female connector 4 at its end. Tape 2 surrounds tubing 11 and tape 12 surrounds tubing 3. Holders 1 and 10 respectively have smooth bolt holes or threaded holes 13 and 6 near their respective flat, mating surfaces. Bolts or screws can be inserted to secure the holders and the connectors, before or after connection is made.

Figure 4A:
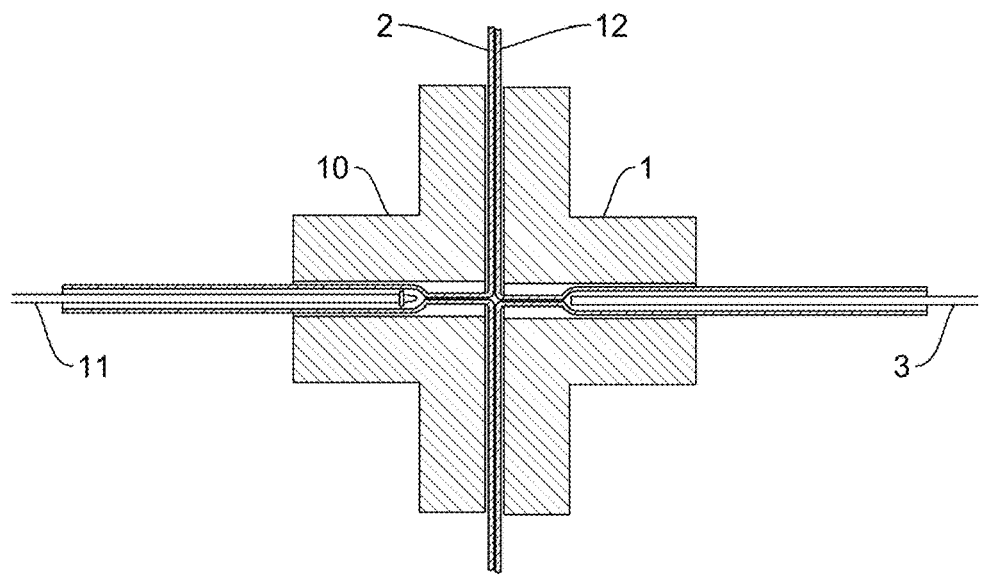
FIG. 4A is a cross-sectional view of the joined holders of FIGS. 1A and 1C, before the connectors are mated.
Figure 4B:
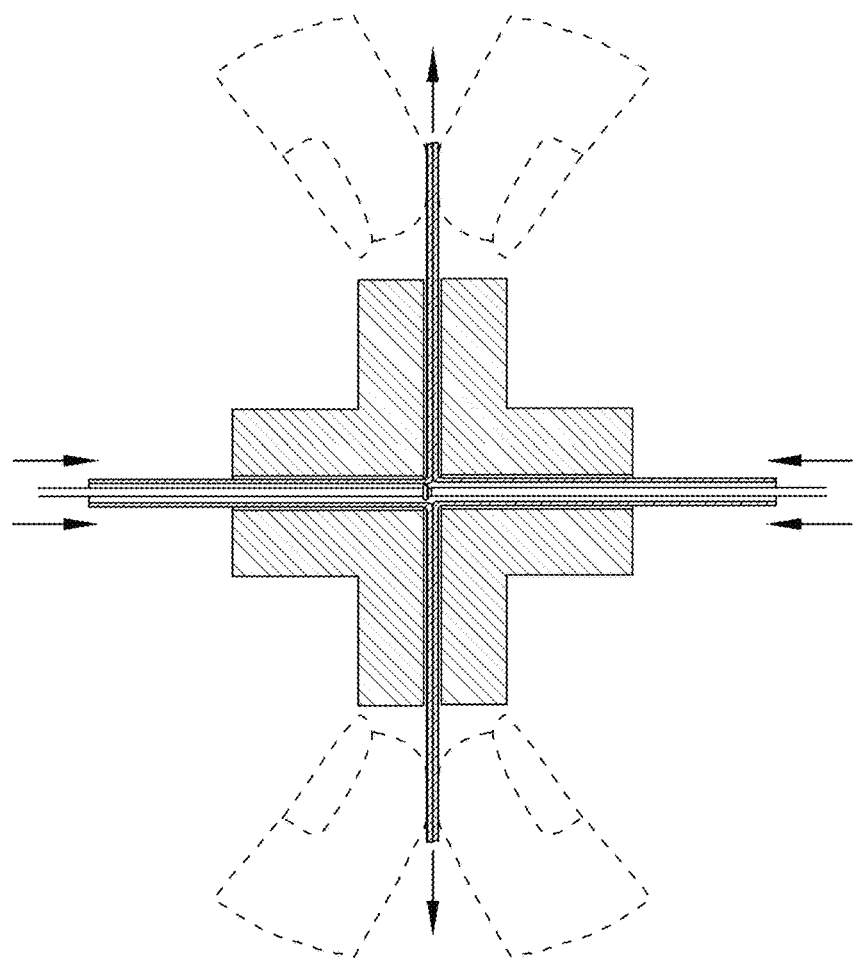
FIG. 4B is a cross-sectional view of the joined holders of FIGS. 1B and 1D, after the connectors are mated.
Figure 5A:
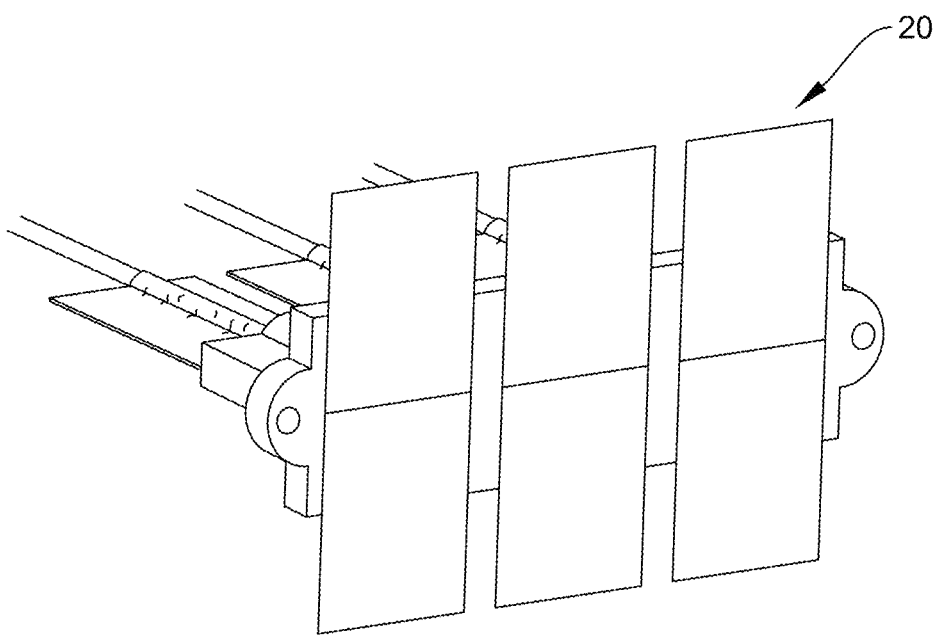
FIG. 5A is an elevational view of an embodiment where a single holder houses three side by side tubings and each tubing is separately taped, showing a connector (which is concealed and could be male or female) before extension.
Figure 5B:
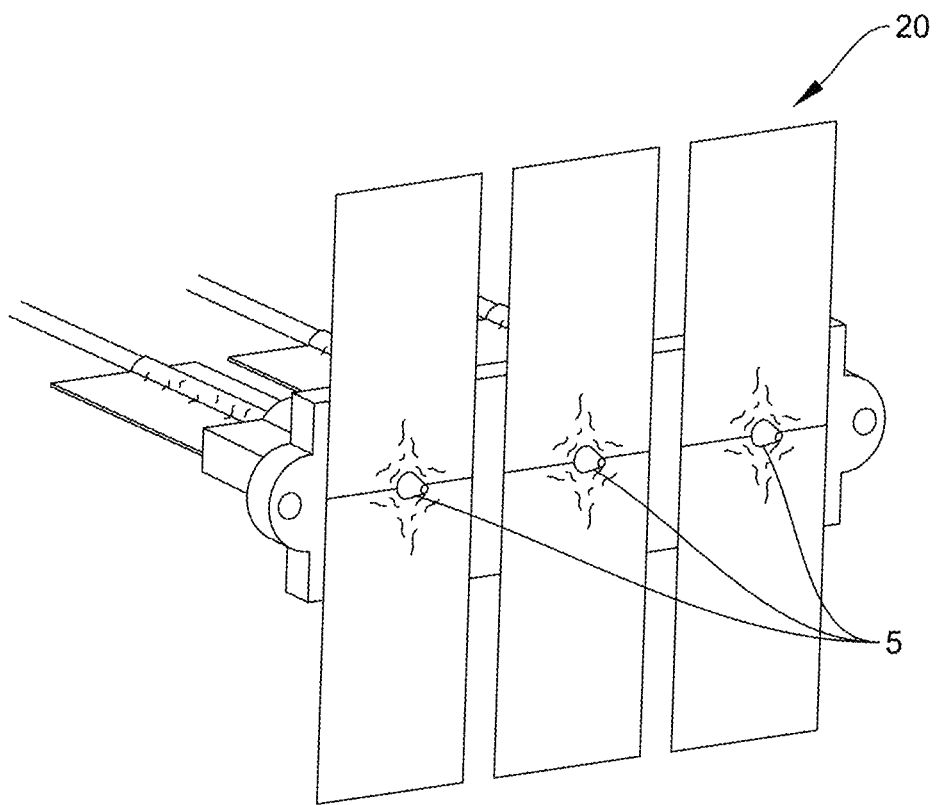
FIG. 5B is an elevational view of the embodiment of FIG. 5A after connector extension, where the connector is a male connector.
Figure 6A:
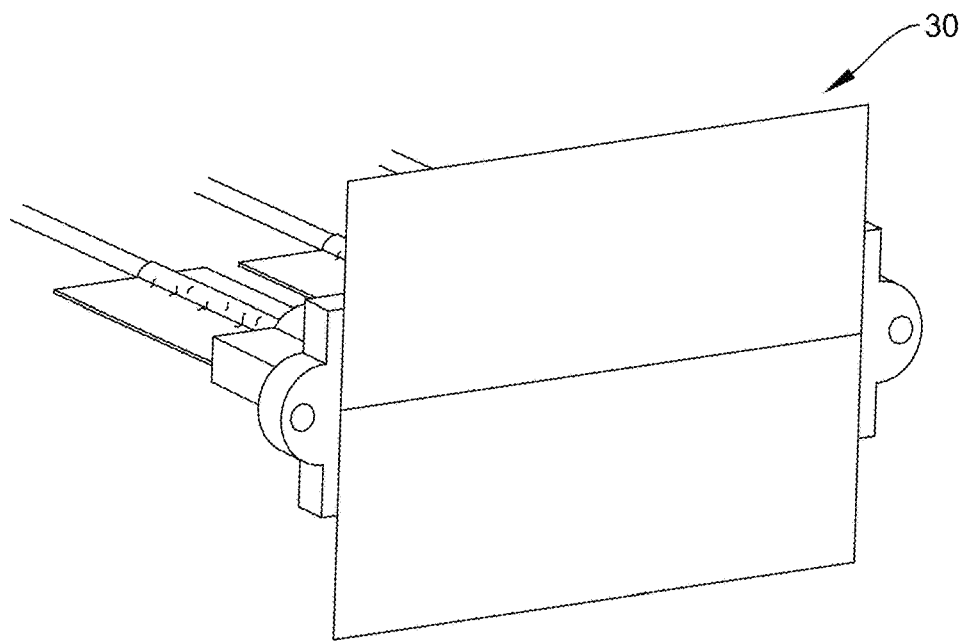
FIG. 6A is an elevational view of an embodiment where a single holder houses three side by side tubing with all tubing commonly taped, showing a connector (which is concealed and could be male or female) before extension.
Figure 6B:
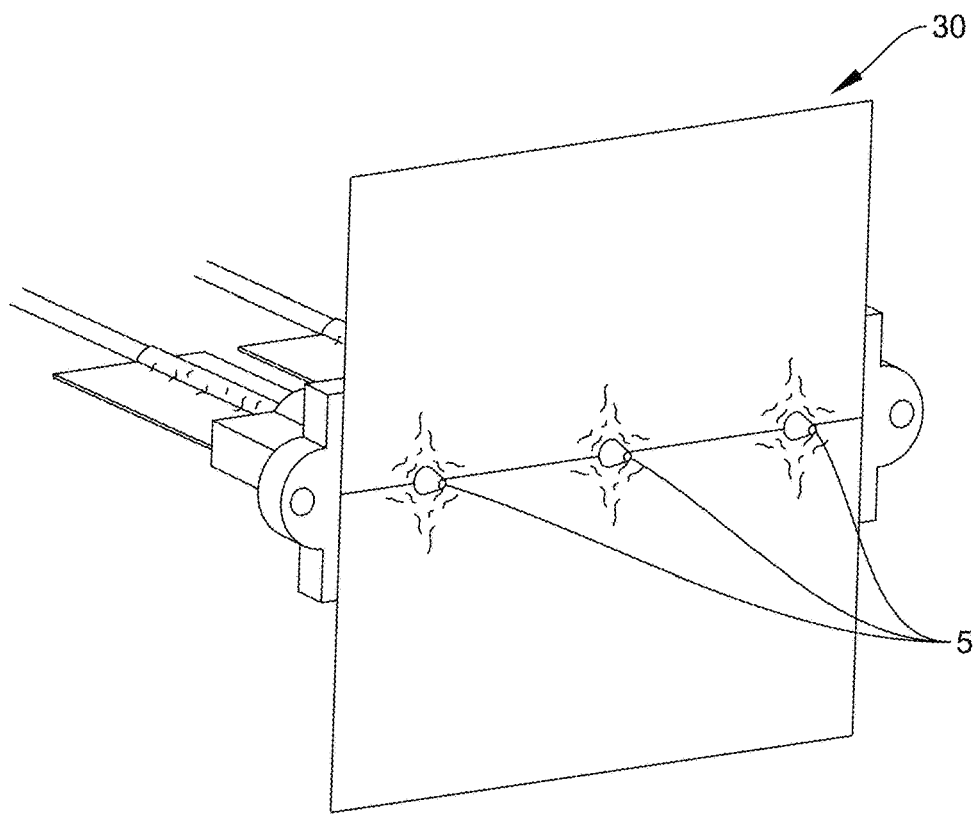
FIG. 6B is an elevational view of the embodiment of FIG. 6A after connector extension, where the connector is a male connector.
Figure 7A:
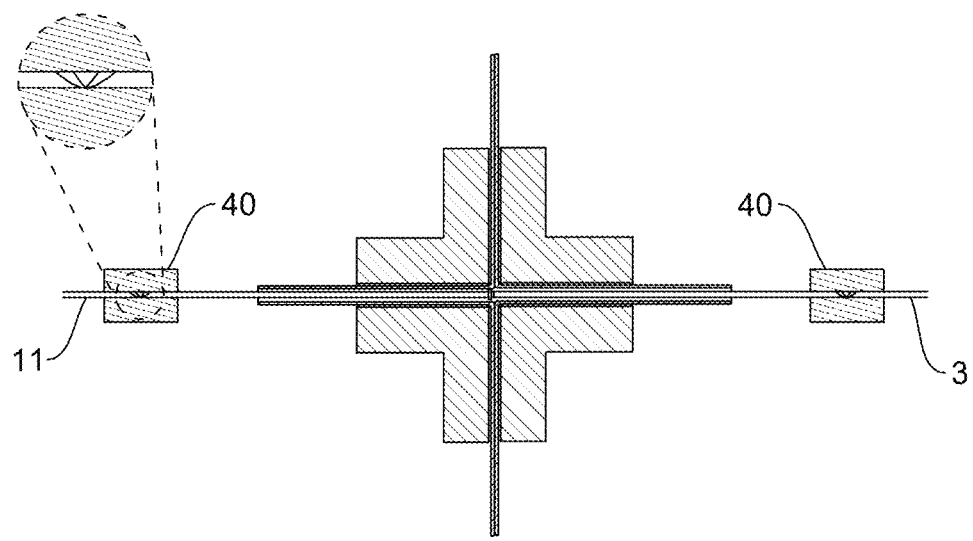
FIG. 7A is a cross-sectional view of a joined holders of the invention with a pinch valve in the tubing which is closed to prevent fluid flow.
Figure 7B:
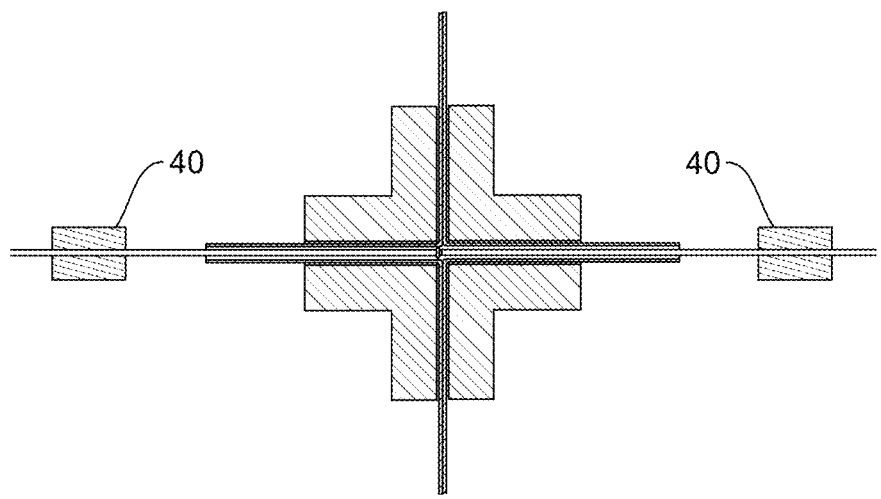
Figure 7C:
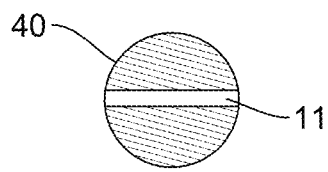
FIG. 7C is an enlarged view of the pinch valve interior showing the valve is open.

FIG. 3 illustrates advancing connector 5 by pulling apart the ends of tape 2 to advance the male connector 5, which lies within the channel in holder 10. FIGS. 4A and 4B show a cross section of the holders 1 and 10 before connection (FIG. 4A) and after connection (FIG. 4B). FIGS. 5A & 5B show a single holder 20 with several female connectors and a single holder with several male connectors, respectively, where each connector is individually taped and can be individually advanced. FIGS. 6A & 6B show a single holder 30 with several female connectors and a single holder with several male connectors, respectively, where all male connectors and all female connectors are collectively taped and connect simultaneously when advanced. FIG. 7A illustrates a closed pinch valve 40 in tubing 11 and tubing 3, which can stop flow to the connectors 4 and 5 prior to connection or prior to disconnecting the mated tubing connectors, to avoid leakage and help maintain sterility, and then be opened to restore flow after connection is made as in FIG. 7B. FIG. 7C shows an enlarged cross-section of pinch valve 40.

Male connector 5 has a central bore and a tapered end, as shown, and may include a barb at the end which secures the connection to female connector 4. Female connector 4 has a central bore and is made of an elastic material, to deform and then tightly accommodate the tapered end of male connector 5, so as to seal the connection and maintain the contents of the tubing in a sterile environment.

Tubing 11 and tubing 3 may have only one length of tape attached to each, rather than the two lengths of tape shown in the figures surrounding the tubing. The end of each length of tape is pulled to advance the respective male and female connectors, and connect them. As shown in the FIGS. 4A and 4B for two lengths of tape, it is convenient to use the edge of the channel in the holder to pull the tape against, such that one pulls transverse to the channel (up or down).

Because the ends of each length of tape are intended to be grabbed and pulled, it is preferred to either not have adhesive in the end regions, or these end regions could have a non-stick backing attached that is gripped and pulled to mate the connectors.

After the connectors are mated, the holders 1 and 10 can be fixed by placing bolts into holes 13 and 6, and adding nuts; or threading in bolts where holes 13 and 6 are threaded. Holders 1 and 10 can also be held in mated position by magnets, straps, elastic straps, or by an interlocking feature on the surface of the opposing holders, including such opposed fixtures which twist and lock together. Following the mating and securing of the connector housings, the tubing connection is made.

Figure 8A:
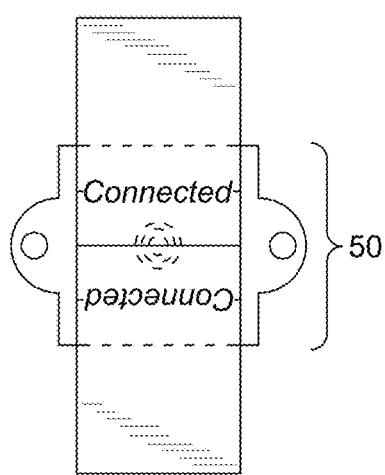
FIG. 8A depicts a connector with a visual indicator (identified with a printed instruction) to be visualized before connection of the connectors.
Figure 8B:
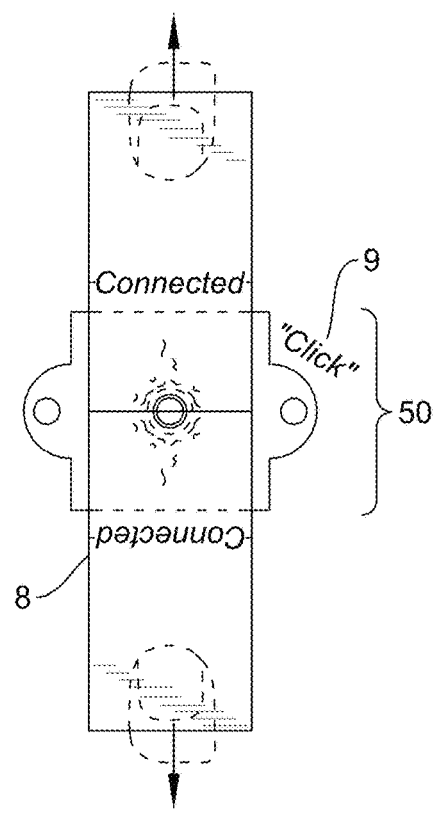
FIG. 8B depicts the connector of FIG. 8A after connection of the connectors.

FIGS. 8A and 8B depict a connector with a visual indicator 50 (identified with a printed instruction) to be visualized before connection of the connectors, before and after connection.

Figure 8C:
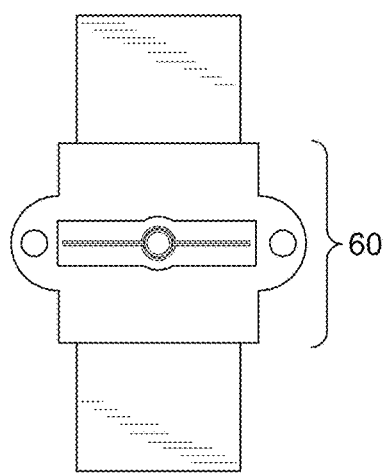
FIG. 8C depicts another embodiment of a connector with a visual indicator which is obstructed before actuation.
Figure 8D:
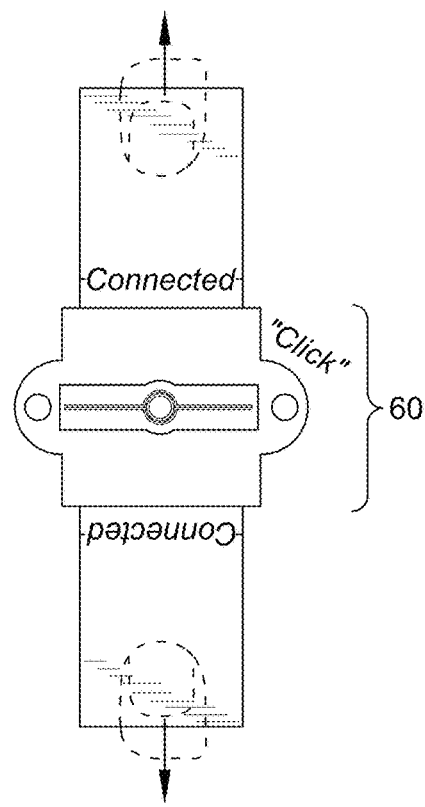
FIG. 8D depicts the connector of FIG. 8C after connection of the connectors, with the visual indicator unobstructed indicating connection was made.

FIG. 8C depicts another embodiment of a connector with a visual indicator 60 which is obstructed before actuation. Visual indicator 60 is unobstructed indicating connection was made, in FIG. 8D.

Figure 9A:
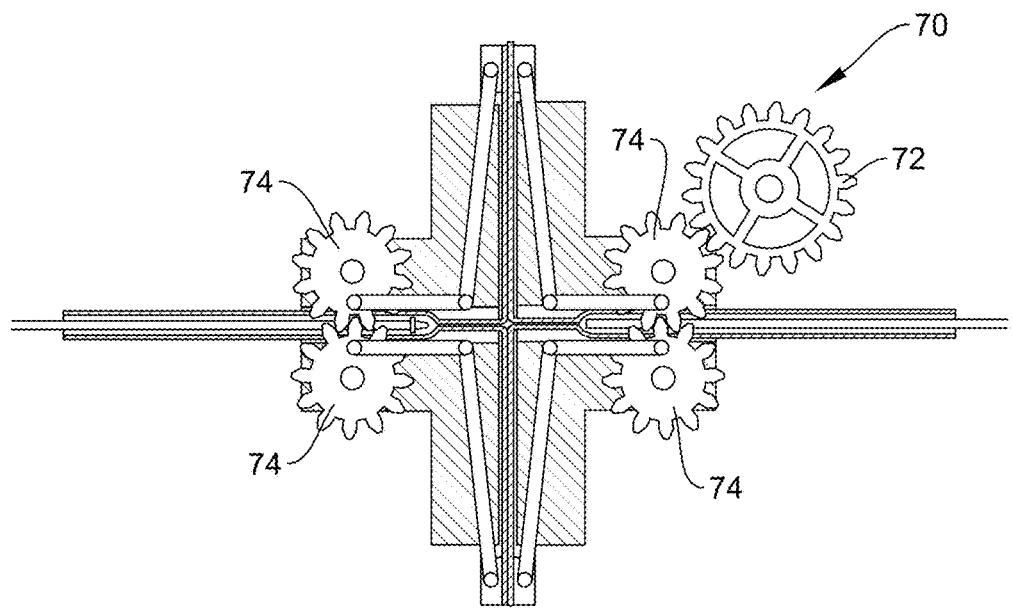
FIG. 9A depicts a mechanism for connecting the connectors with a single mechanical motion rather than the two motions, required to pull the tabs, with the connectors shown before connection.
Figure 9B:
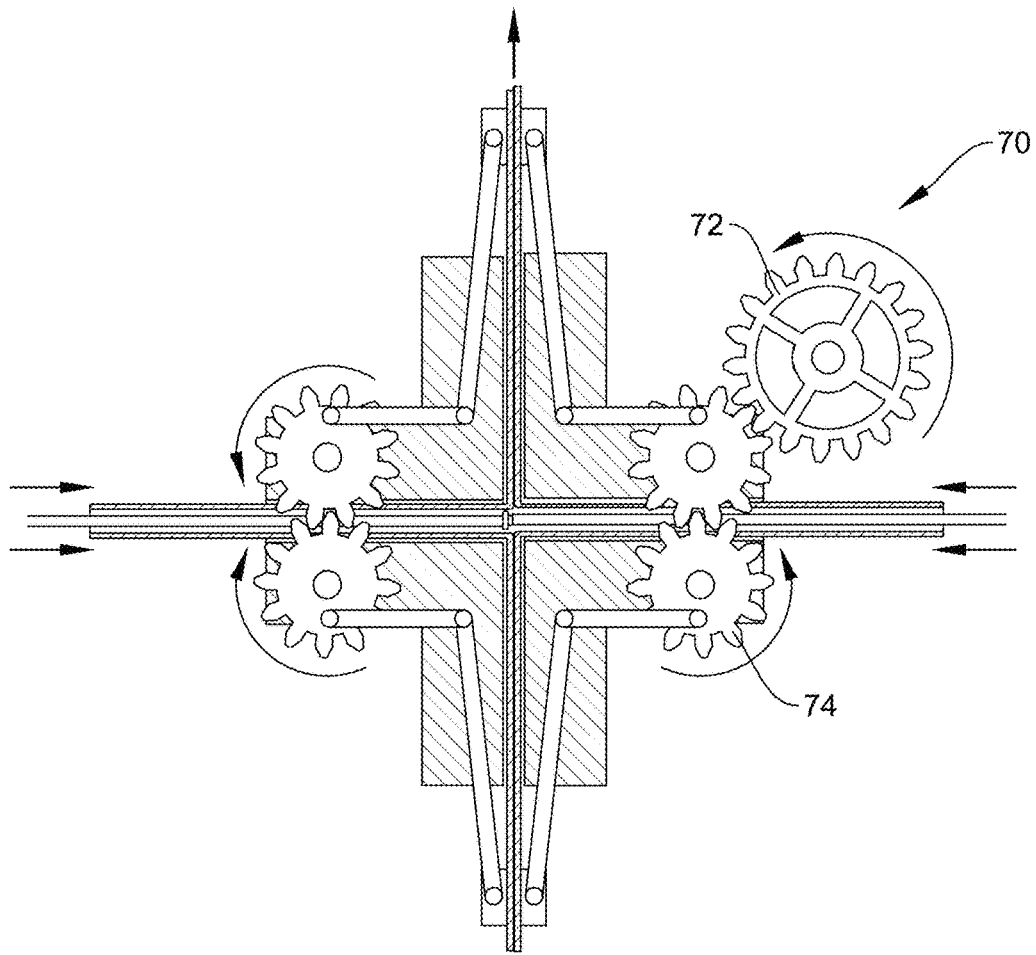
FIG. 9B depicts the mechanism of FIG. 9A after connection.

FIGS. 9A & 9B depict a mechanism 70 for connecting the connectors connection with a single mechanically driven action rather than pulling the tabs opposite. Mechanism 70 has a main drive gear 72 which can be powered by electromechanical means, allowing for robotic automation of the connection. Main drive gear 72 drives gears 74 as shown, to advance the tape between gears 74 and the connectors towards each other to the position shown in FIG. 9B.

Figure 10A:
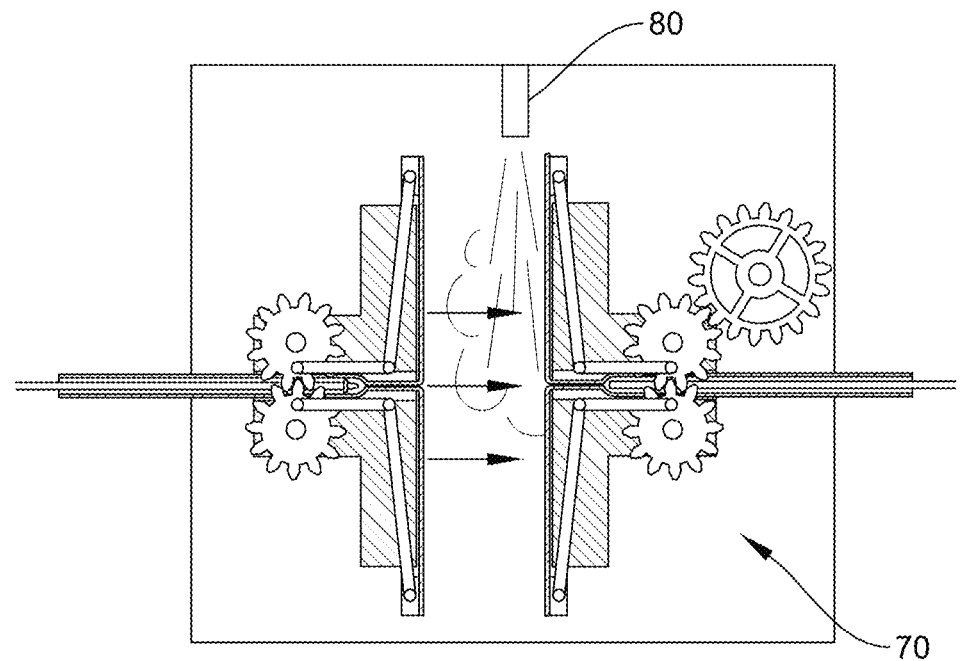
FIG. 10A depicts an additional sterilisation procedure which can be included before joining the holders.
Figure 10B:
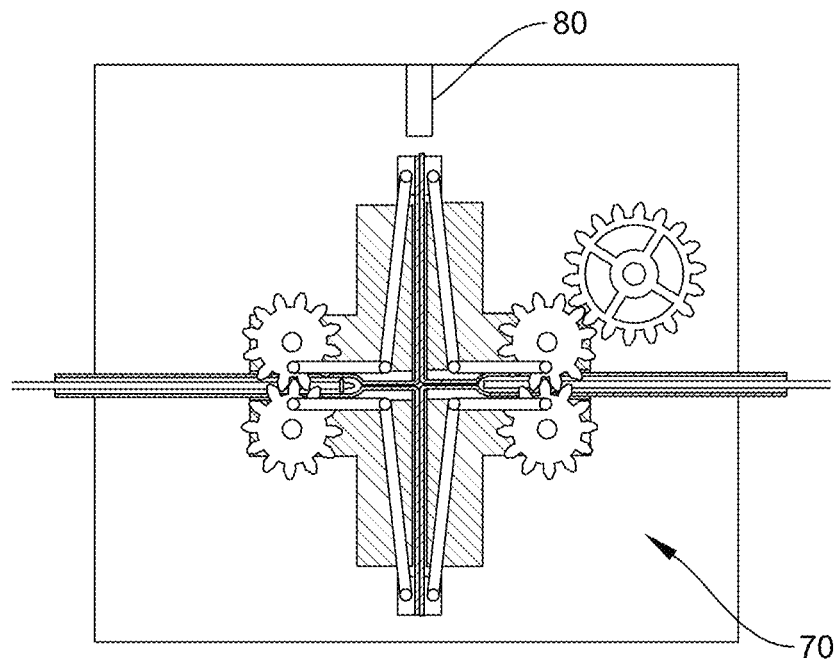
FIG. 10B depicts the joined holders of FIG. 10A.

FIGS. 10A & 10B depict a sterilization procedure for mechanism 70 and the connectors, tubing etc. with it. Where the operation of the device or where necessary configurations of the connectors reduce the sterility or application requirements, that may necessitate increased efforts to rid the device of contaminants, additional to that which the taped sealing and connection method alone provide. Sterilization can be achieved with means such as steam, ethylene gas (or similar) or atomised liquid sterilising agent, entering through port 80. Furthermore, sterilization can be conducted in an enclosed environment alongside robotic automation, permitted by mechanism 70, to further enhance the sterility of the setup.

A number of features of this system minimise the risk of contamination of the fluid within the tubing, and maintain sterility. The holders and all portions of the system should be subject to regular sterilisation procedures, such as steam, or atomised sterilising agents.

- As the tubing ends were sealed in a sterile environment inside the tape prior to connection, the tubing is kept sterile;
- The housing provides an additional barrier for contaminants, enclosing the connection interface.
- There is minimal exposure of the open ends of the tubing to the atmosphere, as they connect immediately following the tape encapsulating the connector being pulled apart.

These features are also applicable in reverse as the connection is broken (by pulling on the tubing either side of the connector) as the tape reseals around each connector as it is pulled into the housing. As the adhesive side of the tape is kept in constant contact with another adhesive side of another section of tape, (with the exception of the region of connection, in which it is surrounded by the housing and conceivably a sealed environment) it is never exposed and is therefore kept contaminant free.

This connector can also be adapted to make use of mechanical coupling as a means of driving actuation. In this way, the action of pulling both ends of tape can be coupled to a single mechanical motion, this can further be adapted by driving this through electromechanical means, in this way an autonomous means of connection can be produced. This has the advantage of allowing the connection to be made within a highly controlled environment, where the risk of contamination can be lowered, this risk can further be lowered with the introduction of sterilisation procedures. By means such as steam, sterilising gas or atomised liquid sterilising agents, the environment and connector itself can be sterilised to further minimise the risk of contamination during both connection and disconnection.

This invention addresses the pressing need for forming a versatile sterile/semi-sterile connection that combines the advantages of aseptic fluid transfer, multiple connections and disconnections, and seamless integration into automated systems. By doing so, it has the potential to advance the state of the art in industries that demand precision, sterility, and efficiency.

The connection method allows a sterile connecting to be made without the use of chemical agents or creating an external sterile environment. This reduces complexity, contamination risk and cost.

The connection method can be readily automated, with a simple mechanism making the connection. Multiple connectors can be connected to the same mechanism to further reduce complexity.

The connection method allows connections to be established and broken multiple times, while maintaining almost the original level sterility, until there is interruption by mechanical failure. This allows fluid networks to be detached for activities such as measurement, replacement of spent reagents or connection for a further manufacturing stage.

The connection method allows establishment of even multiple sterile connections with a few steps. The connection method can readily be scaled and there is no need for chemical agents at any scale. The ability to break and remake the connection reduces any potential need for redundant pathways at scale, which would be proportionally more expensive.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising" and "including" are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of connecting a first tubing to a second tubing for aseptic fluid transfer, comprising:
    providing two holders each with a channel designed to house the first or second tubing and each with a mating surface at one end of the channel;
    attaching a male connector having a central bore and a tapered distal end to a female connector having a central bore that is an elastic material designed to surround the male connector and form a seal, wherein the male connector has the tapered distal end furthest from the first tubing when the first tubing is connected to a proximal end of the male connector and the female connector has a first end furthest from the second tubing when a second end of the female connector is connected with the second tubing;
    placing the first tubing in the channel in the first holder and the second tubing in the channel in the second holder such the respective male and female connectors are opposing each other;
    attaching a first tape with adhesive on one surface to a portion of the first tubing, wherein the first tape has sufficient length to extend past the distal end of the male connector and has no adhesive on the surfaces which extend from the distal end of the male connector to an end of the first tape;
    attaching the second tape with adhesive on one side to a portion of the second tubing, wherein the second tape has sufficient length to extend past the first end of the female connector and has no adhesive on the surfaces which extend from the end of the female connector to an end of the second tape; and placing the mating surfaces of the holders adjacent and pulling the ends of the first tape and the second tape such that the male connector and the female connector advance towards each other, and the male connector is pulled inside the female connector and forms the seal and provides a fluid connection from the first tubing to the second tubing.

2. The method of claim 1 further including attaching a third tape with adhesive on one surface to a portion of the male connector and to a portion of the first tubing such that said third tape opposes said first tape, and adhering the adhesive surface of said third tape to the opposed adhesive surface of the first tape;

attaching a fourth tape with adhesive on one surface to a portion of the female connector and a portion of the second tubing such that said fourth tape opposes said second tape, and adhering the adhesive surface of said fourth tape to the opposed adhesive surface of the second tap; and pulling the ends of the first tape and the third tape apart and pulling the ends of the second tape and the fourth tape apart so that the male connector is pulled inside the female connector.

3. The method of claim 1 further including fastening the two holders using bolts, screws, magnets, straps, elastic straps or adhesive, or opposed fixtures which twist and lock together.

4. The method of claim 1 wherein a visual, auditory or tactile feedback indicates when the connection is made.

5. The method of claim 1 further comprising a pinch valve on the first or second tubing to prevent fluid flow to the male or female connector before the connection is made.

6. The method of claim 1 further comprising a mechanism to pull the ends of the first tape and the second tape to establish the connection.

7. The method of claim 6 further comprising a robotic mechanism that automatically pulls the ends of the first tape and the second tape to establish the connection.

8. The method of claim 1 further comprising connecting a plurality of first and second tubings to form multiple fluid networks.

9. The method of claim 1 wherein the first and second holders include a flexible layer on the mating surfaces, which are pressed together to form a seal.

10. The method of claim 1 wherein the connection is made or broken autonomously, triggered by a detected external event.

11. The method of claim 1 further comprising an autonomous sterilisation procedure.

12. The method of claim 11 further including a secondary sterilisation procedure using an aerosolized or gaseous sterilisation applied to the connector to further reduce the risk of contamination.

13. The method of claim 12 wherein sterilisation is performed using steam, atomised ethanol or ethylene gas.

14. The method of claim 1 wherein the method is used in applications that require the connection between two tubings be performed in a controlled environment.

15. The method of claim 14 wherein the applications include: cell and gene therapy applications, stem cell therapy, regenerative medicine and tissue engineering applications, cell banking applications, pharmaceutical manufacturing applications, bio-manufacturing and biotechnology research applications, cell expansion applications, cell culture bioprocessing applications, and chemical processing applications.

* * * * *